United States Patent [19]

O'Donnell et al.

[11] Patent Number: 5,554,753

[45] Date of Patent: Sep. 10, 1996

[54] CATALYTIC ENANTIOSELECTIVE SYNTHESIS OF α-AMINO ACID DERIVATIVES BY PHASE-TRANSFER CATALYSIS

[75] Inventors: Martin J. O'Donnell, Indianapolis, Ind.; Shengde Wu, Urbana, Ill.; Irena Esikova, El Cerrito, Calif.; Aiqiao Mi, Chengdu, China

[73] Assignee: Indiana University Foundation, Bloomington, Ind.

[21] Appl. No.: 111,661

[22] Filed: Aug. 25, 1993

[51] Int. Cl.[6] .................. C07D 487/08; C07D 471/08
[52] U.S. Cl. ................................. 546/134; 546/126
[58] Field of Search ........................... 546/134, 126

[56] References Cited

PUBLICATIONS

"Chemical & Engr. News" Apr. 10, 1989 pp. 25–27.
I. Algranati "J. Bio. et Biophys. Acta" (1963) vol. 73 p. 154.

*Primary Examiner*—David B. Springer
*Attorney, Agent, or Firm*—Woodard, Emhardt, Naughton, Moriarty & McNett

[57] ABSTRACT

Described are improved processes for the enantioselective synthesis of α-amino acids which involve combinations of solvents, highly-mixed and low-temperature reaction conditions, and novel catalysts. Also described are novel catalysts and precursors to α-amino acid derivatives.

7 Claims, 2 Drawing Sheets

RATE OF PTC ALKYLATION: EFFECT OF STIRRING RATE AND RELATIVE AMOUNT OF AQUEOUS SODIUM HYDROXIDE

TEMPERATURE DEPENDENCE STUDIES

| Temp °C. | $r_0 \times 10^{-4}$ Ms$^{-1}$ | $E^{\ddagger}_{obs}$ cal/mol | % ee |
|---|---|---|---|
| 34.5 | 7.6 | | 62 |
| 30.5 | 8.4 | 250.4 | 62 |
| 25.5 | 7.9 | | 62 |
| 19.5 | 8.3 | | 64 |
| 11.0 | 7.7 | | 62 |
| 0 | 4.0 | 8939 | 68 |

$$\Delta H = E^*_{high} - E^*_{low} = -9.2 \text{ kcal/mol.}$$

$$r_0 = \frac{kB[HA]_0[RBr]_0[QX]_0[NaOH]_0}{1 + B[RBr]_0[HA]_0 \{[QX]_0 + [NaOH]_0\}} \quad \text{where } B = K_{eq}\left(\frac{k_1}{k + k_2}\right)$$

1. Complex character of the rate constant
   $k_{obs} = f(k, K_{eq}, k, k_2)$
2. Exothermic process

CATALYTIC ENANTIOSELECTIVE SYNTHESIS OF α-AMINO ACID DERIVATIVES BY PHASE-TRANSFER CATALYSIS

This invention was made with government support under National Institute of Health Grant No. GM 28193 entitled "Schiff Base Synthons in Amino Acid Chemistry". The U.S. Government has certain rights in this invention.

BACKGROUND OF THE INVENTION

The present invention relates generally to enantioselective processes for preparing α-substituted or α,α-disubstituted amino acid derivatives, and more particularly to such processes achieving improved enantioselectivity and catalysts for the same.

As further background, the utilization of natural and unnatural α-amino acids in practically all areas of the physical and life sciences continues to grow. In addition to their key biological role as the "building blocks" of peptides, proteins and other natural products, the α-amino acids are used extensively in the pharmaceutical, agrochemical and food industries.

They have also been used in total synthesis and other synthetic studies, both as sources of chirality in final products and as chiral auxiliaries, reagents and catalysts for asymmetric synthesis. Because of this widespread use, new and versatile methods for both the small and large scale preparation of natural as well as structurally diversified α-amino acid derivatives are important. Methods for the asymmetric synthesis of α-amino acids that involve catalytic enantiocontrol are one area of interest. See, generally, "Synthesis of Optically Active α-Amino Acids," R. M. Williams, Pergamon, Oxford, 1989.

In the area of carbon-carbon bond formation involving the reaction of α-anionic synthons of glycine or higher amino acids, a synthesis of α-monoalkyl amino acids using catalytic phase-transfer (PTC) alkylations of the benzophenone imine of certain glycine alkyl esters and other glycine synthons has been reported. M. J. O'Donnell, J. M. Boniece and S. E. Earp, Tetrahedron Lett., 1978, 2641; M. J. O'Donnell and T. M. Eckrich, Tetrahedron Lett., 1978, 4625; L. Ghosez, J.-P. Antoine, E. Defense, M. Navarro, V. Libert, M. J. O'Donnell, W. A. Bruder, K. Willey and K. Wojciechowski, Tetrahedron Lett., 1982, 23, 4255.

As advantages, in contrast to known anhydrous alkylative routes, the PTC method involves a simple reaction procedure, mild conditions, inexpensive and safe reagents and solvents, commercially available starting substrates and the ability to easily scale-up the reaction. Since there was no chirality control element used in these early reactions, the products are racemic mixtures (50:50 mixture of two enantiomers). The method has been extended to the alkylation of certain aldimine derivatives as a route to α,α-dialkyl amino acids (here exemplified by a racemic synthesis of certain α-methyl amino acids). M. J. O'Donnell, B. LeClef, D. B. Rusterholz, L. Ghosez, J.-P. Antoine and M. Navarro, Tetrahedron Lett., 1982, 23, 4259; M. J. O'Donnell and D. B. Rusterholz, Synth. Commun., 1989, 19, 1157. These phase transfer alkylations have been conducted under a variety of mild, basic conditions (M. J. O'Donnell, J. M. Boniece and S. E. Earp, Tetrahedron Lett., 1978, 2641; M. J. O'Donnell and T. M. Eckrich, Tetrahedron Lett., 1978, 4625; L. Ghosez, J.-P. Antoine, E. Defense, M. Navarro, V. Libert, M. J. O'Donnell, W. A. Bruder, K. Willey and K. Wojciechowski, Tetrahedron Lett., 1982, 23, 4255; M. J. O'Donnell, W. Bruder, K. Wojciechowski, L. Ghosez, M. Navarro, F. Sainte and J.-P. Antoine, Peptides: Structure and Function, Proc. 8th Amer. Pept. Symp., 1983, 151; M. J. O'Donnell, K. Wojciechowski, L. Ghosez, M. Navarro, F. Sainte and J.-P. Antoine, Synthesis, 1984, 313.) and other interesting amino acids, such as 1-aminocyclopropane-1-carboxylic acid, (M. J. O'Donnell, W. A. Bruder, T. M. Eckrich, D. F. Schullenberger and G. S. Staten, Synthesis, 1984, 127.) and 3-fluorophenylalanine (M. J. O'Donnell, C. L. Barney and J. R. McCarthy, Tetrahedron Lett., 1985, 26, 3067.) have been prepared using this procedure.

An asymmetric synthesis of α-amino acids by phase-transfer catalysis (PTC) was reported by M. J. O'Donnell, W. D. Bennett and S. Wu, J. Am. Chem. Soc., 1989, 111, 2353 [see "Phase-Transfer Catalysis Offers Practical α-Amino Acid Synthesis," Chemical & Engineering News, Apr. 10, 1989, pages 25–27 for an article about this paper]. The methodology developed using early catalytic systems allowed preparation of either enantiomer of a several types of target amino acids in up to 66% enantiomeric excess ("ee") (an 83:17 mixture of enantiomers). The method used catalytic amounts of pseudoenantiomeric phase-transfer catalysts 1 and 2. These catalysts and their precursors, cinchonine and cinchonidine, respectively, are inexpensive and commercially available.

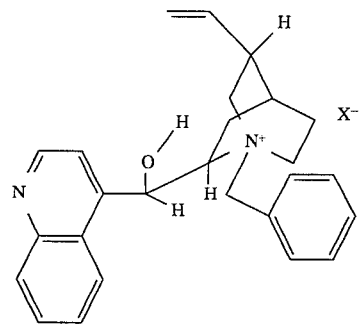

(from cinchonine)

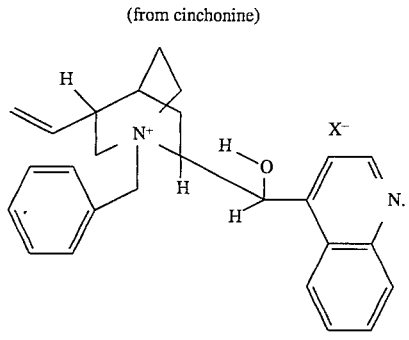

(from cinchonidine)

The ability to scale the reaction up and the possibility of preparing α-amino acids in good optical purity were demonstrated by the synthesis of 6.5 g of optically pure non-natural 4-chloro-D-phenylalanine (R-4, R=4-ClC$_6$H$_4$CH$_2$) from the starting substrate 3 (R'=tBu). M. J. O'Donnell, W. D. Bennett and S. Wu, J. Am. Chem. Soc., 1989, 111, 2353 [see "Phase-Transfer Catalysis Offers Practical α-Amino Acid Synthesis," Chemical Engineering News, Apr. 10, 1989, pages 25–27 for an article about this paper]. By changing from the cinchonine- (1) to the cinchonidine-derived catalyst series (2), the optically pure enantiomeric product (S-4, R'=4ClC$_6$H$_4$CH$_2$) could also be prepared by this procedure.

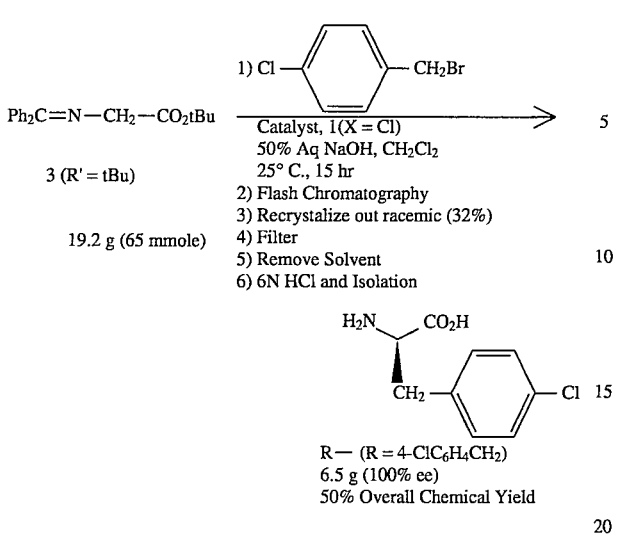

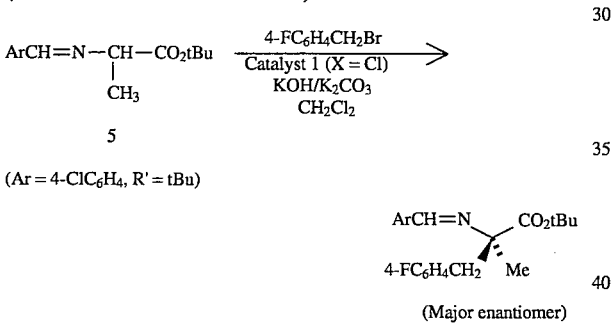

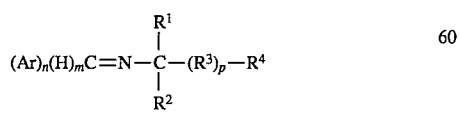

(Major enantiomer)

The PTC methodology has recently been extended to the synthesis of α-methyl amino acids (M. J. O'Donnell and S. Wu, *Tetrahedron: Asymmetry*, 1992, 3, 591.), an important class of unnatural amino acid derivatives. For example, 5 (Ar=4-ClC$_6$H$_4$, R'=tBu) was alkylated with 4-fluorobenzyl bromide in the presence of a catalytic amount of N-benzylcinchoninium chloride (1, X=Cl) to give the α-methyl-4-fluoro-R-phenylalanine derivative in 50% enantioselectivity (75:25 mixture of enantiomers).

A review of enantioselective syntheses in the presence of phase transfer catalysts is found in M. J. O'Donnell, "Asymmetric Phase Transfer Reactions," in *Catalytic Asymmetric Synthesis*, I. Ojima, Ed., VCH, New York, 1993.

In light of this background there remain needs for improved processes for producing α-amino acid derivatives, catalysts providing improved enantioselectivity, and precursors to α-amino acid derivatives. The present invention addresses these needs.

SUMMARY OF THE INVENTION

Accordingly, one preferred embodiment of the invention provides a process for enantioselectively preparing a compound of the formula:

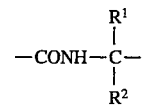

wherein:
  n is 1 or 2, and m is 0 when n is 2 and 1 when n is 1;
  p is 0, 1 or 2;

Ar is aryl up to C$_{30}$;
R$^1$ is —H; C$_1$ to C$_{10}$ alkyl, alkenyl or alkynyl each optionally substituted with carboxyl, C$_1$ to C$_5$ alkoxy, amino (i.e. —NH$_2$), mono- or dialkylamino wherein the alkyl is C$_1$ to C$_5$, hydroxyl, —SH, or —S—alkyl wherein the alkyl is C$_1$ to C$_5$; aryl up to C$_{30}$ or C$_1$ to C$_5$ alkyl-aryl up to C$_{30}$ each optionally Ar-substituted with halogen, hydroxyl, nitro, C$_1$ to C$_5$ alkyl, C$_1$ to C$_5$ alkoxy, benzyloxy, or C$_1$ to C$_5$ fluoroalkyl; or —CH$_2$—R wherein R is 3-indolyl optionally ring-substituted with halogen, hydroxyl, C$_1$ to C$_5$ alkyl, C$_1$ to C$_5$ alkoxy, benzyloxy, or C$_1$ to C$_5$ fluoroalkyl; or 4-imidazolyl; with the proviso that when R$^1$ is other than —H, n and m are each 1;

R$^2$ is C$_1$ to C$_{10}$ alkyl, alkenyl or alkynyl each optionally substituted with carboxyl, C$_1$ to C$_5$ alkoxy, fluoro, amino, mono- or dialkylamino wherein the alkyl is C$_1$ to C$_5$, —OH, —SH, —S—alkyl wherein the alkyl is C$_1$ to C$_5$; aryl up to C$_{30}$ or alkyl-aryl wherein the alkyl is C$_1$ to C$_5$ and optionally fluoro-substituted and the aryl is up to C$_{30}$, each aryl optionally being Ar-substituted with halogen, hydroxyl, nitro, C$_1$ to C$_5$ alkyl, C$_1$ to C$_5$ alkoxy, benzyloxy, or C$_1$ to C$_5$ fluoroalkyl; or —CH2—R$^5$ wherein R$^1$ is 3-indolyl optionally ring-substituted with halogen, hydroxyl, C$_1$ to C$_5$ alkyl, C$_1$ to C$_5$ alkoxy, benzyloxy, or C$_1$ to C$_5$ fluoroalkyl; or 4-imidazolyl;

R$^1$ and R$^2$ are optionally protected at any acidic nitrogen, oxygen or sulfur atoms;

R$^3$ is a group of the formula

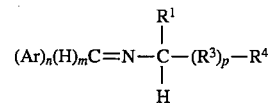

wherein R$^1$ and R$^2$ are defined as above; and
R$^4$ is cyano or protected carboxyl.
The process comprises reacting a compound of the formula $$(Ar)_n(H)_mC=N-\underset{\underset{H}{|}}{\overset{\overset{R^1}{|}}{C}}-(R^3)_p-R^4$$

with a compound of the formula R$^2$—X where X is a leaving group, under basic conditions in the presence of an enantioselective phase transfer catalyst in a solvent comprising an aromatic solvent and a halogenated C$_1$ to C$_5$ alkane solvent.

Another preferred embodiment of the invention provides an enantioselective catalyst comprising an N-substituted O-substituted cinchoninium or cinchonidinium halide or a 3a,3b-dihydro N-substituted O-substituted cinchoninium or cinchonidinium halide, wherein the N-substituent is alkyl-aryl wherein the alkyl is C$_1$ to C$_5$ and the aryl is up to C$_{30}$, and the O-substituent is C$_1$ to about C$_{10}$ alkyl or alkenyl.

Another preferred embodiment of the invention provides a compound of the formula:

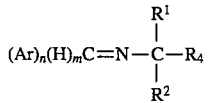

wherein:
  Ar is an aryl up to C$_{30}$;
  n is 1 or 2, and m is 0 when n is 2 and 1 when n is 1;
  R$^1$ is —H; C$_1$ to C$_{10}$ alkyl, alkenyl or alkynyl each optionally substituted with carboxyl, C$_1$ to C$_5$ alkoxy, amino (i.e. —NH$_2$), mono- or dialkylamino wherein the alkyl is C$_1$ to C$_5$, hydroxyl, —SH, or —S—alkyl wherein the alkyl is C$_1$ to C$_5$; aryl up to C$_{30}$ or C$_1$ to C$_5$ alkyl-aryl up to C$_{30}$ each optionally Ar-substituted with halogen, hydroxyl, nitro, C$_1$ to C$_5$ alkyl, C$_1$ to C$_5$ alkoxy, benzyloxy, or C$_1$ to C$_5$ fluoroalkyl; with the proviso that when R$^1$ is other than —H, n and m are each 1;

R$^2$ is —CH$_2$—R$^4$ wherein R$^4$ is 3-indolyl, optionally ring-substituted with halogen, nitro, hydroxy, C$_1$ to C$_5$ alkyl, C$_1$ to C$_5$ alkoxy, or benzyloxy;

R$^1$ and R$^2$ are optionally protected at any acidic nitrogen, oxygen or sulfur atoms; and R$^4$ is cyano or protected carboxyl.

Another preferred embodiment of the invention provides a process for preparing a compound of the formula:

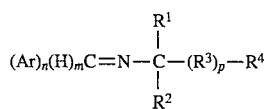

wherein:

Ar is an aryl up to C$_{30}$;

n is 1 or 2, and m is 0 when n is 2 and 1 when n is 1;

p is 0, 1 or 2;

R$^1$ is —H; C$_1$ to C$_{10}$ alkyl, alkenyl or alkynyl each optionally substituted with carboxyl, C$_1$ to C$_5$ alkoxy, amino (i.e. —NH$_2$), mono- or dialkylamino wherein the alkyl is C$_1$ to C$_5$, hydroxyl, —SH, or —S—akyl wherein the alkyl is C$_1$ to C$_5$; aryl up to C$_{30}$ or C$_1$ to C$_5$ alkyl-aryl up to C$_{30}$ each optionally Ar-substituted with halogen, hydroxyl, nitro, C$_1$ to C$_5$ alkyl, C$_1$ to C$_5$ alkoxy, benzyloxy, or C$_1$ to C$_5$ fluoroalkyl; or —CH$_2$—R$^5$ wherein R$^5$ is 3-indolyl optionally ring-substituted with halogen, hydroxyl, C$_1$ to C$_5$ alkyl, C$_1$ to C$_5$ alkoxy, benzyloxy, or C$_1$ to C$_5$ fluoroalkyl; or 4-imidazolyl; with the proviso that when R$^1$ is other than —H, n and m are each 1;

R$^2$ is a C$_1$ to C$_{10}$ alkyl, alkenyl or alkynyl group; and

R$^3$ is a group of the formula

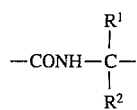

wherein R$^1$ and R$^2$ are defined as above; and

R$^4$ is cyano or protected carboxyl.

The process comprises reacting a compound of the formula

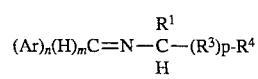

with an excess of liquid compound of the formula R$^2$—X where X is a leaving group, under basic conditions in the presence of a phase transfer catalyst and in the absence of another solvent.

A still further embodiment of the invention provides a process for preparing a compound of the formula:

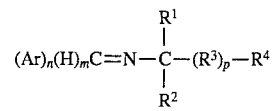

wherein:

n is 1 or 2, and m is 0 when n is 2 and 1 when n is 1;

p is 0, 1 or 2;

Ar is aryl up to C$_{30}$;

R$^1$ is —H; C$_1$ to C$_{10}$ alkyl, alkenyl or alkynyl each optionally substituted with carboxyl, C$_1$ to C$_5$ alkoxy, amino (i.e. —NH2), mono- or dialkylamino wherein the alkyl is C$_1$ to C$_5$, hydroxyl, —SH, or —S—akyl wherein the alkyl is C$_1$ to C$_5$; aryl up to C$_{30}$ or C$_1$ to C$_5$ alkyl-aryl up to C$_{30}$ each optionally Ar-substituted with halogen, hydroxyl, nitro, C$_1$ to C$_5$ alkyl, C$_1$ to C$_5$ alkoxy, benzyloxy, or C$_1$ to C$_5$ fluoroalkyl; or —CH$_2$—R$^5$ wherein R$^5$ is 3-indolyl optionally ring-substituted with halogen, hydroxyl, C$_1$ to C$_5$ alkyl, C$_1$ to C$_5$ alkoxy, benzyloxy, or C$_1$ to C$_5$ fluoroalkyl, or 4-imidazolyl; with the proviso that when R$^1$ is other than —H, n and m are each 1;

R$^2$ is C$_1$ to C$_{10}$ alkyl, alkenyl or alkynyl each optionally substituted with carboxyl, C$_1$ to C$_5$ alkoxy, fluoro, amino, mono- or dialkylamino wherein the alkyl is C$_1$ to C$_5$, —OH, —SH, —S—akyl wherein the alkyl is C$_1$ to C$_5$; aryl up to C$_{30}$ or alkyl-aryl wherein the alkyl is C$_1$ to C$_5$ and optionally fluoro-substituted and the aryl is up to C$_{30}$, each aryl optionally being Ar-substituted with halogen, hydroxyl, nitro, C$_1$ to C$_5$ alkyl, C$_1$ to C$_5$ alkoxy, benzyloxy, or C$_1$ to C$_5$ fluoroalkyl; or —CH2—R$^5$ wherein R$^5$ is 3-indolyl optionally ring-substituted with halogen, hydroxyl, C$_1$ to C$_5$ alkyl, C$_1$ to C$_5$ alkoxy, benzyloxy, or C$_1$ to C$_5$ fluoroalkyl; or 4-imidazolyl;

R$^1$ and R$^2$ are optionally protected at any acidic nitrogen, oxygen or sulfur atoms;

R$^3$ is a group of the formula

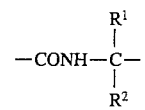

wherein R$^1$ and R$^2$ are defined as above; and

R$^4$ is cyano or protected carboxyl.

The process comprises reacting a compound of the formula

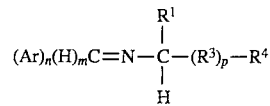

with a compound of the formula R$^2$—X where X is a leaving group, under basic conditions in the presence of an enantioselective phase transfer catalyst in a reaction medium under mixing conditions sufficient to achieve a reaction rate of at least about 0.5×10$^{-4}$ moles per second.

DESCRIPTION OF THE PREFERRED EMBODIMENT

Figures 1A, 1B:
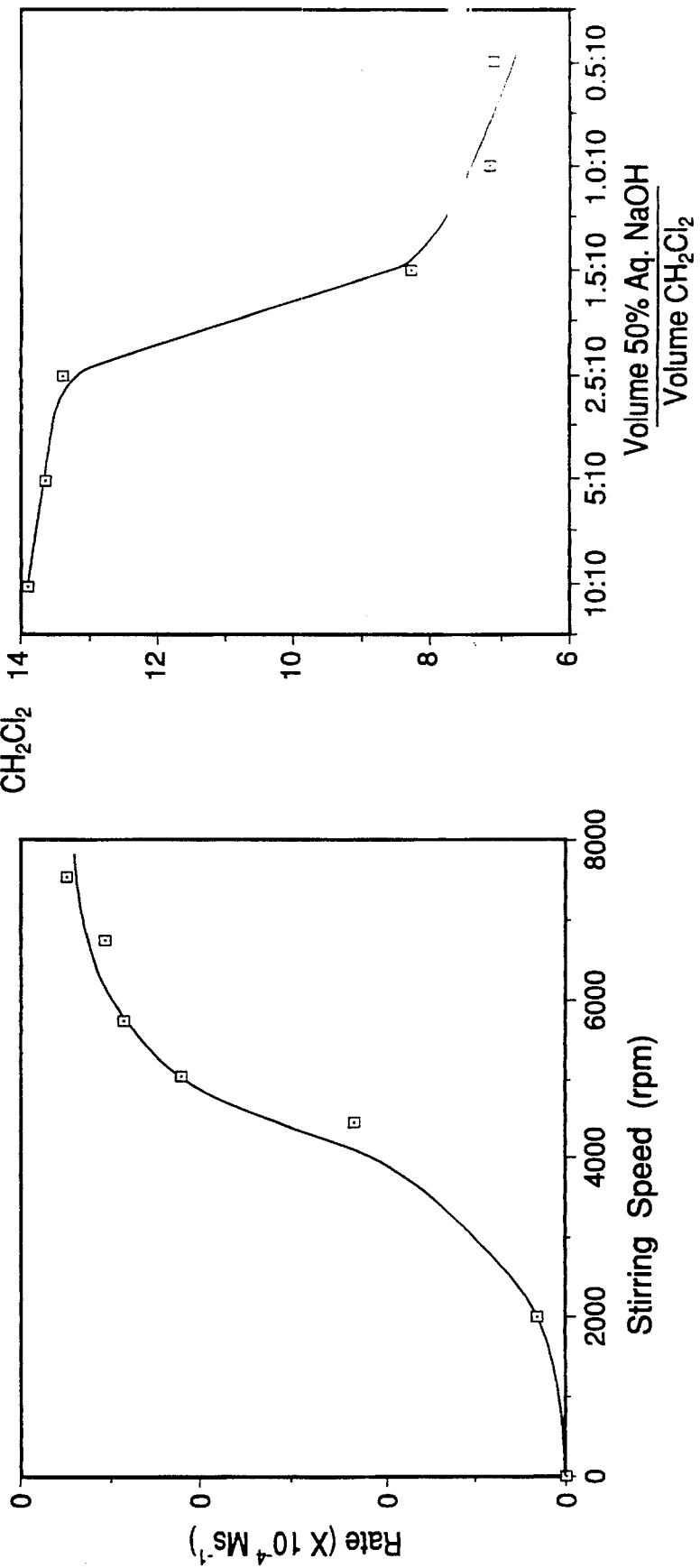

For the purposes of promoting an understanding of the principles of the invention, reference will now be made to certain preferred embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention pertains.

The present invention provides processes which can be used to prepare amino acids and modified amino acids with enantioselectivity. Thus, products formed by inventive processes include those encompassed by formula I:

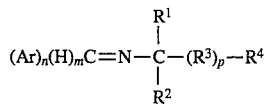

wherein:

n is 1 or 2, and m is 0 when n is 2 and 1 when n is 1;

p is 0, 1 or 2;

Ar is aryl up to $C_{30}$;

$R^1$ is —H; $C_1$ to $C_{10}$ alkyl, alkenyl or alkynyl each optionally substituted with carboxyl, $C_1$ to $C_5$ alkoxy, amino (i.e. —$NH_2$), mono- or dialkylamino wherein the alkyl is $C_1$ to $C_5$, hydroxyl, —SH, or —S—akyl wherein the alkyl is $C_1$ to $C_5$; aryl up to $C_{30}$ or $C_1$ to $C_5$ alkyl-aryl up to $C_{30}$ each optionally Ar-substituted with halogen, hydroxyl, nitro, $C_1$ to $C_5$ alkyl, $C_1$ to $C_5$ alkoxy, benzyloxy, or $C_1$ to $C_5$ fluoroalkyl; or —$CH_2$—R5 wherein $R^5$ is 3-indolyl optionally ring-substituted with halogen, hydroxyl, $C_1$ to $C_5$ alkyl, $C_1$ to $C_5$ alkoxy, benzyloxy, or $C_1$ to $C_5$ fluoroalkyl; or 4-imidazolyl; with the proviso that when $R^1$ is other than —H, n and m are each 1;

$R^2$ is $C_1$ to $C_{10}$ alkyl, alkenyl or alkynyl each optionally substituted with carboxyl, $C_1$ to $C_5$ alkoxy, fluoro, amino, mono- or dialkylamino wherein the alkyl is $C_1$ to $C_5$, —OH, —SH, —S—akyl wherein the alkyl is $C_1$ to $C_5$; aryl up to $C_{30}$ or alkyl-aryl wherein the alkyl is $C_1$ to $C_5$ and optionally fluoro-substituted and the aryl is up to $C_{30}$, each aryl optionally being Ar-substituted with halogen, hydroxyl, nitro, $C_1$ to $C_5$ alkyl, $C_1$ to $C_5$ alkoxy, benzyloxy, or $C_1$ to $C_5$ fluoroalkyl; or —$CH_2$—$R^5$ wherein $R^5$ is 3-indolyl optionally ring-substituted with halogen, hydroxyl, $C_1$ to $C_5$ alkyl, $C_1$ to $C_5$ alkoxy, benzyloxy, or $C_1$ to $C_5$ fluoroalkyl; or 4-imidazolyl;

$R^1$ and $R^2$ are optionally protected at any acidic nitrogen, oxygen or sulfur atoms;

$R^3$ is a group of the formula

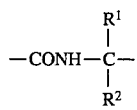

wherein $R^1$ and $R^2$ are defined as above; and $R^4$ is cyano or protected carboxyl.

As is well known by those practiced in the area, when manipulating compounds such as those of formula I, it is often desired to protect at acidic nitrogens, sulfurs or oxygen groups in the molecule. The protecting groups can be those which are conventionally used in solid-phase peptide synthesis (BOC or FMOC strategies) or solution-phase peptide synthesis (CBz strategy). Thus, suitable protecting groups for acidic nitrogens include formyl, [4-toluenesulfonyl(Tos)] [t-butyloxycarbonyl(Boc)] 2,4-dinitrophenol, benzyloxymethyl, triphenylmethyl (trityl), t-butoxymethyl, 2-chlorobenzyloxy-carbonyl, allyloxycarbonyl, benzyloxycarbonyl (Z), mesitylene-2-sulfonyl, 4-methyloxy-2,3,6-trimethyl- benzyenesulfonyl, 2,2,5,7,8-pentamethyl-chroma n-6-sulfonyl, (9-xanthenyl), (triphenylmethyl (trityl)) and 2,4,6-trimethoxybenzyl. Suitable protecting groups for acidic sulfur groups include 4-methylbenzyl, 3-nitro-2-pyridinesulfenyl, triphenylmethyl (trityl), 2, 4,6-trimethoxybenzyl, acetamidomethyl, trimethylacetaminomethyl, t-butylsulfonyl and sulfoxide. To protect acidic oxide groups, suitable protecting groups include benzyl ether, t-butyl ether, benzyl ether, 2,6-dichlorobenzyl ether, 2-bromobenzyl ether, and 3,5-dibromobenzyl ether. It will be understood that the skilled artisan will be able to select and utilize protecting groups in appropriate instances and that the use of protecting groups is within the spirit and scope of the present invention.

It is preferred that at least one of $R^1$ and $R^2$ is a side chain in a naturally-occurring amino acid. Thus, preferred groups $R^1$ and $R^2$ include those of the formulas —H, —$CH_3$, —$CH(CH_3)_2$, —$CH_2$—$CH(CH_3)_2$, —$CH(CH_3)$—$CH_2$—$CH_3$, —$CH_2$-phenyl, —$CH_2$-p-hydroxyphenyl, —$CH_2$-3-indolyl, —$(CH_2)_4$—$NH_2$, —$(CH_2)_3$—NH—C(NH)—$NH_2$, —$CH_2$-4-imidazolyl, —$CH_2COOH$, —$(CH_2)_2$—COOH, —$CH_2$—$CONH_2$, —$(CH_2)_2$—$CONH_2$, $CH_2$—SH, —$CH_2(OH)$, —$CH(CH_3)(OH)$, and —$(CH_2)_2$—S—$CH_3$. It is also preferred that at least one of $R^1$ and $R^2$ is —H, $C_1$ to $C_{10}$ alkyl (e.g. methyl, ethyl, propyl, butyl, etc.) or benzyl.

Processes of the invention can also be applied to short peptides (i.e. where p is 1 or 2) in which case the adjacent amino acids can be the same or different from one another. Such peptides react in a similar fashion to singular amino acids as demonstrated by D. F. Shullenberger, "Preparation of Schiff Base-Protected Amides and Peptide Derivatives from the Corresponding Tetrabutylammonium Salts" and V. V. Khau, "Selective Alkylation of Protected Schiff Base Dipeptide Derivatives by Catalytic Phase Transfer Alkylations" (both published Master's Theses at Indiana University-Purdue University at Indianapolis, Indianapolis, Ind.).

Suitable aryl groups Ar in formula I generally have up to about 30 carbon atoms (i.e. up to $C_{30}$ aryl). Suitable aryl groups thus include phenyl, naphthyl, and anthracenyl, and phenanthrenyl. Aryl groups such as these, having up to about 15 carbon atoms and up to three fused rings, are preferred. Groups Ar suitable for use in the invention can include one or more heteroatoms (e.g. N, S or O), and/or may be Ar-substituted, for example including one or more substituents (optionally protected where appropriate) selected from the group alkyl, alkenyl, alkynyl (these usually being up to $C_{10}$), $C_1$ to $C_5$ alkoxy, amino, mono- or dialkyl amino wherein the alkyl is usually $C_1$ to $C_5$, benzyl, halo, hydroxy, and nitro. These and other equivalent non-interfering substituents are well known and their presence on groups Ar in formula I is within the scope of the present invention.

As indicated in formula I above, $R^4$ is cyano or a protected carboxyl. In this regard, protected carboxyl includes, for example, carboxyls which are protected as esters (i.e. —$COOR^6$ wherein $R^6$ is usually $C_1$ to $C_{10}$ alkyl, up to $C_{30}$ aryl or alkyl-aryl wherein the alkyl is $C_1$ to $C_5$ and the aryl is up to $C_{30}$ (these can be Ar-substituted as defined for aryl and alkyl-aryl in $R^1$ and $R^2$ above) or as carboxamide groups (i.e. —$CONR^7R^8$ wherein $R^7$ and $R^8$ can be —H or groups such as those for $R^6$). The use of these and similar protective strategies for carboxyl groups is well known and will be practiced by those skilled in the art without undue burden.

In accordance with the invention, compounds of formula I are prepared by reacting a compound of formula II

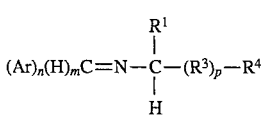

with a compound of the formula $R^2$—X where X is a leaving group. In this regard, suitable leaving groups will be those which are displaced under the conditions of the reaction so as to allow the formation of compounds of formula I. Suitable such leaving groups include halogen (especially chlorine, bromine or iodine), acetate, cyano, and sulfur-containing leaving groups, for example sulfates or tosylates. Among these, the halogens are generally preferred.

Processes of the invention will be conducted in the presence of a catalytic amount of a suitable enantioselective phase transfer catalyst, preferably a quaternary salt derivative of a Cinchona or Ephedra alkaloid. For example, quaternary salt derivatives of Cinchonine, Cinchonidine, Quinidine, Quinine, (+)-Ephedrine, (−)-Ephedrine or (+)-Pseudoephedrine are suitable.

Preferred catalysts for use in the invention are N-subsitituted O-substituted Cinchoninium or Cinchodinium halides of the formula

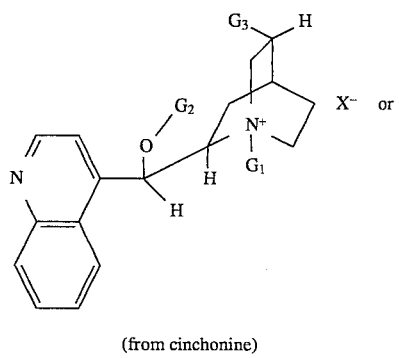

(from cinchonine)

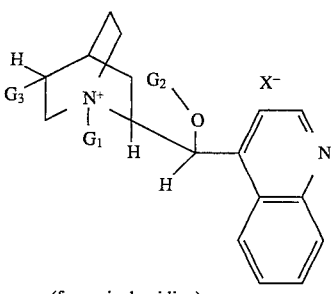

(from cinchonidine)

wherein X is halogen and $G^1$ and $G^2$ are generally organic groups containing up to about 30 carbon atoms. $G^1$ preferably contains an aromatic group, and thus particularly preferred groups $G^1$ include alkyl-aryl groups wherein the alkyl is about $C_1$ to about $C_{10}$ and the aryl is up to about $C_{30}$ (e.g. benzyl or —$CH_2$-naphthyl). Groups $G^1$ in accordance with the invention can also be Ar-substituted with non-interfering substituents (protected where appropriate), for example $C_1$ to $C_5$ alkyl or fluoroalkyl (e.g. p-trifluoromethyl benzyl), alkenyl, or alkynyl, $C_1$ to $C_5$ alkoxy, amino, mono- or dialkylamino where the alkyl is $C_1$ to $C_5$, halogen, hydroxy, nitro, benzyloxy, and the like. These and similar non-interfering substituents are well known and their presence on aromatic rings in $G^1$ is encompassed by the present invention.

In processes of the invention, cinchonine-derived catalysts will generally provide enantiomeric-enriched products of R absolute configuration at the α-carbon (i.e. the carbon between the carboxyl group and the amino group of the amino acid structure). On the other hand, cinchonidine-derived catalysts will generally provide enantiomeric-enriched products of S absolute configuration at the α-carbon.

$G^2$ can be —H or any of the above-specified groups for $G^1$. Particularly preferred catalysts which form another preferred embodiment of the invention, occur where $G^2$ is $C_1$ to $C_{10}$ alkyl or alkenyl, for example methyl, ethyl, propyl, butyl, or allyl.

As indicated, inventive processes will be conducted under basic conditions, and will have an aqueous and an organic phase (i.e. liquid-liquid PTC reactions) or only an organic phase (i.e. solid-liquid PTC reactions). Any suitable base can be used to provide basic conditions. Preferred bases include alkali or alkaline earth metal hydroxides or carbonates or their combinations, for example, sodium hydroxide, potassium hydroxide or $K_2CO_3$ (optionally in combination with $K_2CO_3$), or metal halides such as cesium fluoride (CsF), or the like. Further, it is preferred that the molar ratio of the base to the compound of formula II be about 10:1 to about 50:1.

In liquid-liquid PTC processes, concentrated aqueous solutions of alkali or alkaline earth metal hydroxides are preferred. For example, it is desirable to use at least 40% solutions of NaOH, more desirably at least 50%. In solid-liquid PTC processes, KOH and $K_2CO_3$ are preferred bases, optionally used in combination with.

In broad aspects of the invention, the organic phase of the process can include any organic solvent which is inert to the catalyst, reactants and products involved so as to allow the production and recovery of the desired products. Suitable solvents thus include aromatic solvents such as benzene and alkyl benzenes (especially mono- or di-alkylbenzenes wherein the alkyl groups are $C_1$ to $C_5$ alkyl, e.g. toluene or xylene) or their halogenated counterparts (e.g. mono- or di-chlorobenzene), halogenated alkane solvents, especially $C_1$ to $C_5$ alkanes, ethers, acetonitrile, and similar non-protic solvents. Aromatic solvents and halogenated alkane solvents are preferred, and in one embodiment of the invention a solvent system including both an aromatic solvent and a halogenated $C_1$ to $C_5$ alkane solvent is employed. In this regard, the aromatic and halogenated alkane solvents can be included in any suitable ratio relative to one another; however, it is preferable that they be present in a ratio of about 60:40 to about 80:20, respectively. Surprisingly, it has been discovered that such combined solvent systems provide processes of dramatically improved enantioselectivity, as demonstrated in the specific Examples below.

Additionally, it has been found that enantioselectivity can be improved by conducting reactions of the invention with cooling, for example to temperatures substantially below ambient temperature, preferably below about 10° C., and more preferably about 0°–5° C. Processes conducted at these cool temperatures are thus another feature of the invention.

In another aspect of the invention, it has been discovered that vigorous mixing of the inventive reactions increases the reaction rate without sacrificing enantioselectivity. Thus, especially advantageous processes are conducted with high levels of mixing to provide reaction rates of at least about $0.5 \times 10^{-4}$ moles per second ($Ms^{-1}$), for example, as is achieved using reactive halides such as benzyl bromide as demonstrated in the Examples below. For example, such effective mixing can be achieved by stirring at a rate of at least 2000 revolutions per minute (rpm's), more preferably at least about 4000 rpm's, and typically in the range of about 4000 to 10000 rpm's, as set out in the specific Examples below.

Products produced in accordance with processes of the invention are generally useful as modified or natural amino acids or peptides, or precursors thereto. A preferred set of compounds forms an additional embodiment of the invention, which compounds are encompassed by formula III:

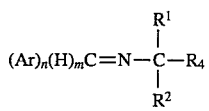

wherein:

Ar is an aryl up to $C_{30}$;

n is 1 or 2, and m is 0 when n is 2 and 1 when n is 1;

$R^1$ is —H; $C_1$ to $C_{10}$ alkyl, alkenyl or alkynyl each optionally substituted with carboxyl, $C_1$ to $C_5$ alkoxy, amino (i.e. —$NH_2$), mono- or dialkylamino wherein the alkyl is $C_1$ to $C_5$, hydroxyl, —SH, or —S—akyl wherein the alkyl is $C_1$ to $C_5$; aryl up to $C_{30}$ or $C_1$ to $C_5$ alkyl-aryl up to $C_{30}$ each optionally Ar-substituted with halogen, hydroxyl, nitro, $C_1$ to $C_5$ alkyl, $C_1$ to $C_5$ alkoxy, benzyloxy, or $C_1$ to $C_5$ fluoroalkyl; with the proviso that when $R^1$ is other than —H, n and m are each 1;

$R^2$ is —$CH_2$—$R^4$ wherein $R^4$ is 3-indolyl, optionally ring-substituted with halogen, nitro, hydroxy, $C_1$ to $C_5$ alkyl, $C_1$ to $C_5$ alkoxy, or benzyloxy;

$R^1$ and $R^2$ are optionally protected at any acidic nitrogen, oxygen or sulfur atoms;

$R^3$ is a group of the formula $$-CONH-\underset{\underset{R^2}{|}}{\overset{\overset{R^1}{|}}{C}}-$$

wherein $R^1$ and $R^2$ are defined as above; and $R^4$ is cyano or protected carboxyl.

Especially preferred are the enantiomers of compounds of formula III having absolute R configuration at the α-carbon. Even more preferably, $R^1$ is $C_1$ to $C_{10}$ alkyl (especially methyl), and $R^3$ is COO-t-butyl. Specifically, where $R^2$ is 3-indolyl and $R^1$ is methyl, the compound provides an intermediate to R-α-methyltryptophan, derivatives of which have recently been discovered to be highly selective and orally active gastrin and CCK-B antagonists with potent anxiolytic properties.

To promote a further appreciation and understanding of the invention and its advantages, the following specific Examples are provided. It will be understood, however, that these Examples are provided by way of illustration and not by way of limitation.

EXPERIMENTAL

SECTION I. PREPARATION AND USE OF CATALYSTS (A) Catalysts 1a–e

Synthesis of O-Benzyl N-Benzyl Cinchonidinium Bromide (1a) (Method A)

To a 100 mL 3-necked round-bottom flask, KH (0.5 g, 8 mmole) and dry THF (10 mL) was added. Cinchonidine (1.18 g, 4 mmole) in dry THF (25 mL) were added slowly. After stirring about 20 minutes, the reaction mixture became a clear orange-yellow solution. At this point, benzyl bromide (2.05 g, 12 mmole) was added dropwise and the reaction mixture was stirred at room temperature for 4 hours. The THF was evaporated in vacuo, the residue was taken into ether 930 mL) and stirred for 10 minutes and filtered. The crude product was recrystallized from methylene chloride-acetone followed by drying in an oven at 100° C. for 24 hours to yield 1.80 g (82%) (m.p. 215°–216° C.).

Synthesis of O-Benzyl N-Benzyl Cinchonidinium Bromide (1a) (Method B).

Cinchonidine (1.18 g, 4 mmole) and methylene chloride (40 mL) were added to a 100 round-bottom flask equipped with a magnetic stirring bar. Benzyl bromide (2.05 g, 12 mmole) was added followed by 50% aqueous NaOH (6.4 g, 80 mmole) in one portion and the resulting mixture was stirred vigorously at room temperature for 4 hours. The mixture was transferred to a separatory funnel, the layers were separated and the methylene chloride layer was washed with water (2×10 mL), dried ($MgSO_4$), filtered and evaporate in vacuo. The crude product was suspended in ether (40 mL), stirred for 4 hours and filtered again. After recrystillization from methylene chloride acetone, 1.90 g (85%) of white crystalline product was obtained (m.p. 214°–215° C.).

The following products were prepared using a procedure identical with that described above for (1a) (Method B).

Synthesis of O-(4-Chlorobenzyl) N-(4-Chlorobenzyl) Cinchonidinium Bromide (1b)

Chemical yield 76%, m.p. 160° C.

Synthesis of O-(4-t-Butylbenzyl) N-(4-t-Butylbenzyl) Cinchonidinium Bromide (1c)

Chemical yield 76%, m.p. 165°–169° C.

Synthesis of O-(2-Naphthylmethyl) N-(2-Naphthylmethyl) Cinchonidinium Bromide (1d)

Chemical yield 84%, m.p. 165°–170° C.

Synthesis of O-Allyl N-Allyl Cinchonidinium Bromide (1e)

Chemical yield 78%, m.p. 105° C. (dec.)

(B) USE OF CATALYSTS 1a–e

Catalysts 1a–e were used in the reaction shown in the Scheme below. The results are given in Table 1.

TABLE 1

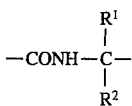

| Catalysts | $C_9$ Config. of Catalyst | Major Enantiomer | % ee | Chem. Yield (%) |
|---|---|---|---|---|
| 1a | R | S | 62% | 80% |
| 1b | R | S | 63% | 83% |
| 1c | R | S | 60% | 70% |
| 1d | R | S | 49% | 72% |
| 1e | R | S | 24% | 76% |

(C) CATALYSTS 2a–n

O-Alkylation of N-benzyl cinchoninium bromide

The procedure for the following products is the same as above for catalysts 1a–e except N-benzyl cinchoninium bromide was used and the reaction time was 3–4 hours. Following chromatographic purification, the products were obtained in chemical yields of 40–84%.

Synthesis of O-methyl N-benzyl cinchoninium bromide (2a)

Chemical yield 42%, m.p. 155°–160° C.

Synthesis of O-ethyl N-benzyl cinchoninium bromide (2b)

Chemical yield 48%, m.p. 145°–150° C.

Synthesis of O-Propyl N-benzyl cinchoninium bromide (2c)

Chemical yield 52%, m.p. 178°–179° C.

Synthesis of O-(n-butyl) N-benzyl cinchoninium bromide (2d)

Chemical yield 48%, m.p. 110° C. (dec.)

Synthesis of O-allyl N-benzyl cinchoninium bromide (2e)

Chemical yield 82%, m.p. 125°–130° C.

Synthesis of O-allyl N-benzyl cinchoninium chloride (2f)

Chemical yield 74%, m.p. 140°–145° C.

Synthesis of O-methallyl N-benzyl cinchoninium chloride (2g)

Chemical yield 75%, m.p. 100° C. (dec.)

Synthesis of O-(3,3'-dimethyallyl) N-benzyl cinchoninium chloride (2h)

Chemical yield 69%, m.p. 140°–144° C.

Synthesis of O-benzyl N-benzyl cinchoninium bromide (2i)

Chemical yield 72%, m.p. 168°–170° C.

Synthesis of O-benzyl N-benzyl cinchoninium chloride (2j)

Chemical yield 64%, m.p. 160°–165° C.

Synthesis of O-(4-chlorobenzyl) N-benzyl cinchoninium bromide (2k)

Chemical yield 76%, m.p. 140°–145° C.

Synthesis of O-(4-t-butylbenzyl) N-benzyl cinchoninium bromide (2l)

Chemical yield 78%, m.p. 145°–150° C.

Synthesis of O-(4-nitrobenzyl) N-benzyl cinchoninium bromide (2m)

Chemical yield 80%, m.p. 192°–193° C.

Synthesis of O-(2-naphthylmethyl) N-benzyl cinchoninium bromide (2n)

Chemical yield 76%, m.p. 160°–164° C.

(D) USE OF CATALYSTS 2a–n

Catalysts 2a–n were used in the reaction shown in the Scheme below. The results are given in Table 2.

TABLE 2

$$Ph_2C=N-CH_2-CO_2tBu \xrightarrow[\substack{CH_2Cl_2 \\ 50\% \text{ NaOH} \\ r.t.}]{PhCH_2Br, \text{ Cat.}} Ph_2C=N\text{-}CH(CH_2Ph)\text{-}CO_2tBu + Ph_2C=N\text{-}CH(CH_2Ph)\text{-}CO_2tBu$$

| Catalysts | C₉ Config. of Catalyst | Major Enantiomer | % ee | Chem. Yield (%) |
|---|---|---|---|---|
| 2a | S | R | 62% | 82% |
| 2b | S | R | 70% | 84% |
| 2c | S | R | 70% | 82% |
| 2d | S | R | 68% | 79% |
| 2e | S | R | 68% | 78% |
| 2f | S | R | 70% | 84% |
| 2g | S | R | 68% | 82% |
| 2h | S | R | 60% | 85% |
| 2i | S | R | 60% | 86% |
| 2j | S | R | 62% | 78% |
| 2k | S | R | 62% | 84% |
| 2l | S | R | 56% | 76% |
| 2m | S | R | 60% | 80% |
| 2n | S | R | 58% | 72% |

SECTION II. SOLVENT-FREE PROCESSES (A) Catalyst effect in enantioselective dialkylation by solid-liquid PTC without solvent (General procedure)

1,1-dimethylethyl N-[(4-chlorophenyl)methylene]-L-alaninate (0.267 g, 1 mmole), O-allyl N-benzyl cinchoninium chloride (2f) (0.046 g, 0.1 mmole), and 1-bromo-2-methylpropane (0.137 g, 10 mmole) were added to a 25 mL round-bottom flask equipped with a magnetic stirring bar. KOH/K₂CO₃ (5/5 mmole, finely ground using a mortor and pestle under argon) was added at once and the resulting mixture was stirred vigorously at room temperature for 18 hours. Methylene chloride (10 m mL) was added and the reaction mixture was filtered to remove solid base, the solids were washed with methylene chloride (2×5 mL) and the solvent was evaporated to dryness on a rotary evaporator. The reside was taken up in ether (20 mL) and the organic solution was washed with water (2×10 mL), dried (MgSO₄), filtered, and evaporated in vacuo to yield 0.24 g (74%) of a yellow oil (optical yield 70% ee, 85% R, 15% S).

The following experiments were carried out using the above described procedure.

Catalyst: O-methyl N-benzyl cinchoninium bromide (2a)

Chemical yield 74%, optical yield 68% ee (84% R, 16% S).

Catalyst: O-ethyl N-benzyl cinchoninium bromide (2b)
Chemical yield 70%, optical yield 68% ee (84% R 16% S).

Catalyst: O-propyl N-benzyl cinchoninium bromine (2c)

Chemical yield 72%, optical yield 69% ee (84.5% R, 5% S).

Catalyst: O-n-butyl N-benzyl cinchoninium bromide (2b)

Chemical yield 72%, optical yield 68% ee (84% R, 16% S)

Catalyst: O-allyl N-benzyl cinchoninium bromide (2e)

Chemical yield 70%, optical yield 68% ee (84% R, 16% S)

Catalyst: O-methallyl N-benzyl cinchoninium chloride (2g)

Chemical yield 70%, optical yield 69% ee (84.5% R, 15.5% S).

Catalyst: O-(3-methyl-2-butenyl) N-benzyl cinchoninium chloride (2h)

Chemical yield 69%, optical yield 56% ee (78% R, 22% S)

Catalyst: O-benzyl-N-benzyl cinchoninium bromide (2i)

Chemical yield 74%, optical yield 58% ee (79% R, 21% S)

Catalyst: O-benzyl N-benzyl cinchoninium chloride (2j)

Chemical yield 75%, optical yield 62% ee (81% R, 19% S)

(B) Enantioselective dialkylation of by solid-liquid PTC without solvent (General Procedure)

1,1-dimethylethyl N-[(4-chlorophenyl)methylene]-L-alaninate (0.267 g, 1 mmole), O-allyl N-benzyl cinchoninium chloride (2g) (0.046 g, 0.1 mmole), and alkyl halide (10 mmole) were added to a 25 mL round-bottom flask equipped with a magnetic stirring bar. $KOH/K_2CO_3$ (5/5 mmole, finely ground using a mortor and pestle under argon) was added at once and the resulting mixture was stirred vigorously at room temperature for 18 hours. Methylene chloride (10 mL) was added and the reaction mixture was filtered to remove solid base, the solids were washed with methylene chloride (2×5 mL) and the solvent was evaporated to dryness on a rotary evaporator. The resin was taken up in ether (20 mL) and the organic solution was washed with water (2×10 mL), dried ($MgSO_4$), filtered, and evaporated in vacuo to yield a yellow oil. Enantiometric excess was determined by HPLC on a chiral column (Baker Bond Chiral OD column) (25 cm×0.46 cm I.K.) No. 21-4-30219) with hexanes at a flow rate of 1.0 mL/min and UV detection at 254 nm).

The above procedure was used to prepare the following products.

Allylation to yield 1,1-dimethylethyl 2-[((4-chlorophenyl)methylene)amino]-2-methyl-R-pentenonate.

1,1-dimethylethyl N-[(4-chlorophenyl)methylene)-L-alaninate (0.267 g, 1 mmole), O-allyl N-benzyl cinchoninium chloride (2f) (0.046 g, 0.1 mole), and allyl bromide (0.123 g, 10 mmole) were stirred vigorously for 18 hours in the presence of $KOH/K_2CO_3$ (5/5 mmole, finely ground using a mortar and pestle under argon).

Chemical yield 85%, optical yield 54% ee (77% R, 23% S).

Isobutylation to yield 1,1-dimethylethyl N-[(4-chlorophenyl)methylene-α-methyl-R-leucinate 1,1-dimethylethyl N-[(4-chlorophenyl)methylene]-L-alaninate (0.267 g, 1 mmole), O-allyl N-benzyl cinchoninium chloride (2f) (0.046 g, 1 mmole), and 1-bromo-2-methylpropane (0.137 g, 10 mmole) were stirred vigorously for 18 hours in the presence of $KOH/K_2CO_3$ (5/5 mmole, finely ground using a mortor and pestle under argon).

Chemical yield 74%, optical yield 70% ee (85% R, 15% S).

Isopropylation to yield 1,1-dimethylethyl N-[(4-chlorophenyl)methylene-α-methyl-R-valinate 1,1-dimethylethyl N-[(4-chlorophenyl)methylene]-L-alaninate (0.267 g, 1 mmole), O-allyl N-benzyl cinchoninium chloride (2f) (0.046 g, 0.1 mmole), and 2-bromopropane (0.123 g, 10 mmole) were stirred vigorously for 18 hours in the presence of $KOH/K_2CO_3$ (5/5 mmole, finely ground using a mortor and pestle under argon).

Chemical yield 60%, optical yield 26% ee (63% R, 37% S).

Isoamylation of to yield 1,1-dimethylethyl 2-[((4-chlorophenyl)methylene)amino]-2-methyl-R-5-methylhexanoate 1,1-dimethylethyl N-[(4-chlorophenyl)methylene[-L-alaninate (0.267 g, 1 mmole), O-allyl N-benzyl cinchoninium chloride (2f) (0.046 g, 0.1 mmole), and 1-bromo-3-methylbutane (0.151 g, 10 mmole) were stirred vigorously for 18 hours in the presence of $KOH/K_2CO_3$ (5/5 mmole, finely ground using a mortor and pestle under argon).

Chemical yield 77%, optical yield 46% e (73% R, 27% S).

Cyclopropylmethylation to yield 1,1-dimethylethyl 2-[((4-chlorophenyl)methylene)amino]-2-methyl-3-cyclopropyl-R-propanoate 1,1-dimethylethyl N-[(4-chlorophenyl)methylene]-L-alaninate (0.267 g, 1 mmole), O-allyl N-benzylcinchonium chloride (2f) (0.046 g, 0.1 mmole), and cyclopropyl bromide (0.135 g, 10 mmole) were stirred vigorously for 18 hours in the presence of $KOH/K_2CO_3$ (5/5 mole, finely ground using a mortor and pestle under argon).

Chemical yield 70%, optical yield 46% ee (73% R, 27%S) Propylation to yield 1,1-dimethylethyl N-[(4-chlorophenyl)methylene]-α-methyl-R-norvalinate.

1,1-dimethylethyl N-[(4-chlorophenyl)methylene]-L-alaninate (0.267 g, 1 mmole), O-allyl N-benzyl cinchoninium chloride (2f) (0.046 g, 0.1 mmole), and 1-bromopropane (0.123 g, 10 mmole) were stirred vigorously for 18 hours in the presence of $KOH/K_2CO_3$ (5/5 mmole, finely ground using a mortor and pestle under argon).

Chemical yield 72%, optical yield 52% ee (76% R, 26% S).

N-butylation to yield 1,1-dimethylethyl N-[(4-chlorophenyl)methylene]-(α-methyl-R-norleucinate 1,1-dimethylethyl N-[(4-chlorophenyl)methylene]-L-alaninate (0.267 g, 1 mmole), O-ally N-benzyl cinchoninium chloride (2f) (0.046 g, 0.1 mmol e), and 1-bromobutane (0.123 g, 10 mole) were stirred vigorously for 18 hours in the presence of $KOH/K_2CO_3$ (5/5 mole, finely ground using a mortor and pestle under argon).

Chemical yield 72%, optical yield 56% ee (78% R, 22% S).

N-Octylation to yield 1,1-dimethylethyl 2-[((4-chlorophenylmethylene)amino]-2-methyl-R-undecanoate 1,1-dimethylethyl N-[(4-chlorophenyl)methylene]-L-alaninate (0.267 g, 1 mmole), O-allyl N-benzyl cinchoninium chloride (2f) (0.046 g, 0.1 mmole), and 1-bromooctane (0.123 g, 10 mole) were stirred vigorously for 18 hours in the presence of $KOH/K_2CO_3$ (5/5 mmole, finely ground using a mortar and pestle under argon).

Chemical yield, –, 54% ee (77% R, 23% S). (Chemical yield and NMR spectra were not obtained since the product was mixture of product and 1-bromooctane).

SECTION III. MIXING AND TEMPERATURE EFFECTS

The experiments set forth in the Scheme below were carried out, and demonstrated that high levels of mixing lead to dramatically increased reaction rates, and that the use of low temperatures provides processes of improved enantioselectivity.

In particular, these experiments demonstrated that the rate of alkylation of 1 in the presence of 50% NaOH and catalyst 6 is highly dependent upon the rate of stirring of the reaction mixture, as shown in FIG. 1A. Moreover, FIG. 1B shows that the ratio of the volumes of the organic and aqueous phases ($v_{org}/v_{aq}$) has an effect on the alkylation rate, with decreased $v_{org}/v_{aq}$ providing increased alkylation rates.

As to temperature, alkylation in the binary solvent containing 70% toluene and 30% methylene chloride showed that chiral induction in the presence of catalyst 6 increased from 70% to 81% when the temperature was decreased from 25° C. to 5° C. while other parameters remained constant.

Figure 2A:
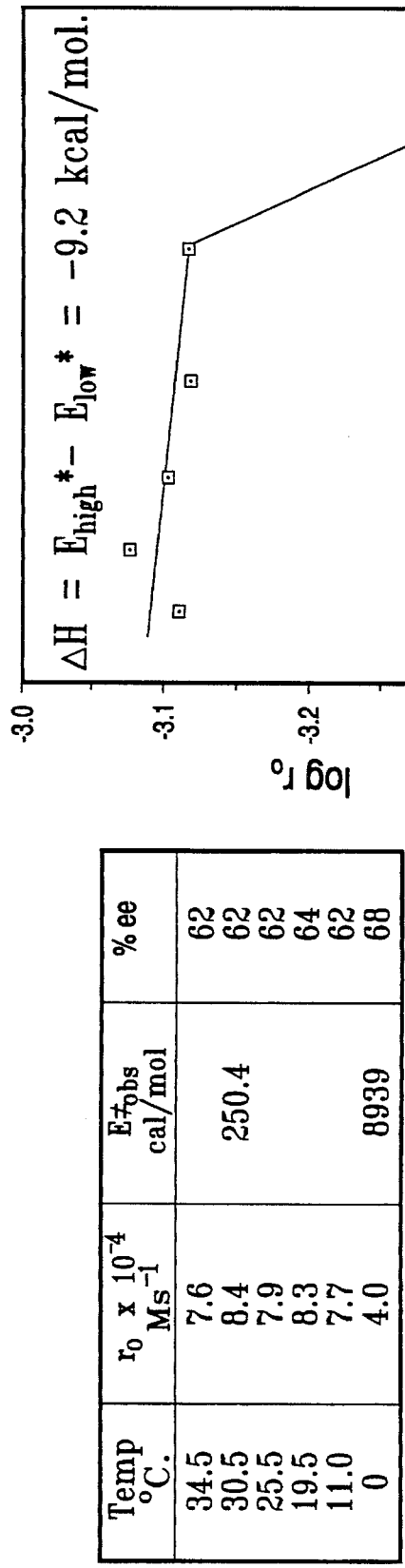
Figure 2B:
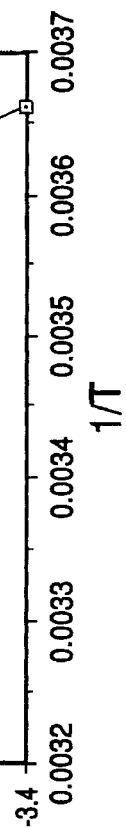

FIGS. 2a and 2b also show the effect of temperature, on both the initial rate of reaction ($r_o$) and the enantioselectivity (%ee). The rate law shown describes the effect of varying the concentrations of the various participants in the reaction: HA=Schiff base substrate; RBr =alkyl halide; QX=phase transfer catalyst; and NaOH=sodium hydroxide base. The complex nature of the rate law equation is believed to be explained by a mechanistic model involving interfacial formation of a tertiary complex (TC) between HA, QX and NaOH (an equilibrium process described by $K_{eq}$). Reaction of TC with RX (described by rate constants $k_1$ and $k_2$, for the forward and reverse reactions, respectively) occurs to form a quaternary complex QC. In the final step of the reaction, complex QC forms product with a rate constant of k. As shown in FIG. 2b, lowering the reaction temperature decreases the initial rate. The enthalpy of formation (H) of OC, which is negative, implying an exothermic process, was estimated from the observed energies of activation at low and high temperature. As also noted from FIG. 2a, lower temperature increases the enantioselectivity of the process.

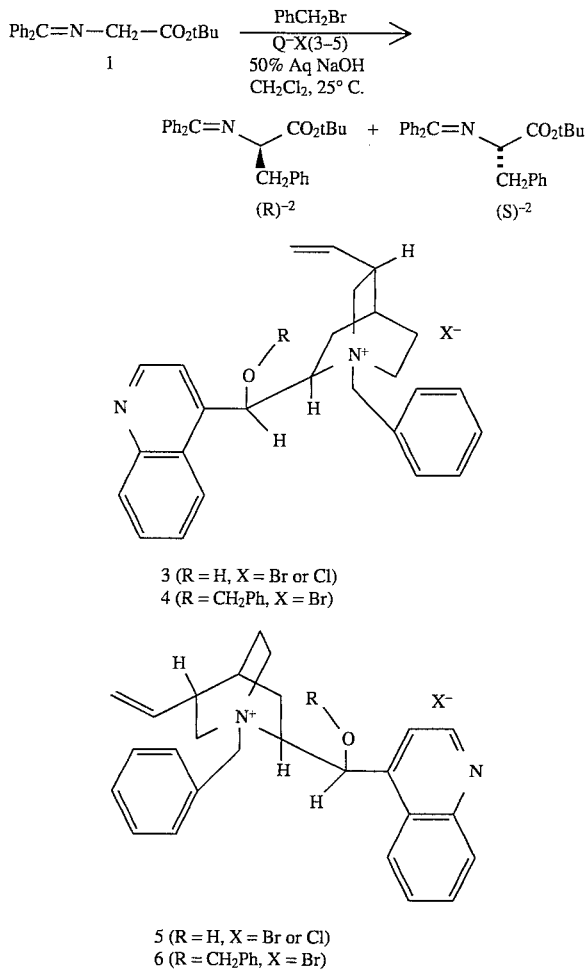

3 (R = H, X = Br or Cl)
4 (R = CH$_2$Ph, X = Br)

5 (R = H, X = Br or Cl)
6 (R = CH$_2$Ph, X = Br)

Materials. N-(diphenylmethylene)glycine tert-butyl ester, benzyl bromide and perylene (used as standard to HPLC analyses) were obtained from Aldrich. The bases NaOH, K$_2$CO$_3$ and KOH were obtained from Mallinckrodt. CsF (99.9%) was obtained from Aldrich. N-Benzylcinchoninium chloride, N-benzylcinchonidinium chloride, cinchonine and cinchonidine were obtained from Fluka. All of the compounds were used without further purification.

The solvents toluene, dichloromethane, tetrahydrofuran and, acetonitrile were HPLC grade and were dried and distilled prior to use. HPLC grade solvents were obtained from the following manufactures: dichloromethane, isopropanol and 1,4-dioxane (Aldrich), acetonitrile (Fisher) and n-hexane (Baker). Distilled and deionized water was used. Tetrahydrofuran, stabilized with 0.025% butylated hydroxytoluene (Mallinckrodt) was distilled from Na/benzophenone prior to use.

Preparation of O,N-dibenzylcinchonidinium bromide (6) and O,N-dibenzylcinchoninium bromide (4). Cinchonine or cinchonidine (2.36 g, 8 mmol) and dichloromethane (80 mL) were added to a 250 mL round-bottom flask equipped with a stirrer. Benzyl bromide (4110 g, 24 mmol) was added followed by 50% aqueous NaOH (12.8 g, 160 mmol) in one portion. The reaction was vigorously stirred at room temperature for 3 hours. The layers were separated and the organic layer was washed once with water (20 mL), dried (MgSO$_4$) and filtered. After evaporation of dichloromethane under vacuum, the crude product was resuspended in anhydrous ether (80 mL). The mixture was stirred for 2 hours and then filtered. Recrystallization of the solid was accomplished from acetone/CH$_2$C$_2$.

Preparation of N-benzylcinchonidinium bromide (5) and N-benzylcinchoninium bromide (3)

Cinchonidine or cinchonine (1.17 g, 4 mmol) and isopropanol were added to a 100 mL round-bottom flask equipped with a stirrer bar and condenser. BEnzyl bromide (0.69 g, 4 mmol) was added in one portion and then the resulting mixture was refluxed for 3 hours. After cooling to room temperature, the precipitate was filtered and washed with isopropanol (2×10 mL). The crude product was recrystallized from hot water and then dried.

Kinetic Procedure

The reaction was a 50 mL three-necked round-bottomed flask submerged in a water bath whose temperature was controlled to ±0.5° C. by a Haake D1 recirculator. Mechanical stirring was performed with a Barnant Model 700-5400 Series 10 Mixer. The impeller of the stirrer was made of Teflon and contained four vertical blades which, during the course of agitation, moved with respect to the center shaft. The agitation rate was measured by a Stewart-Warner Model 757-W hand tachometer.

Initial products were dissolved in solvent and were added to the reactor. The start of the reaction was measured after addition of base to organic layer. Samples (0.1 mL) were removed from the reactor and added to a quench solution containing equal volumes n-hexane and 1,4-dioxane (0.7 mL)

The concentrations of initial Schiff base, O-Benzylated product an benzophenone were monitored by HPLC assay. Enantiomer composition of the O-alkylated product was monitored by chiral HPLC.

Analysis of reaction mixture

HPLC was performed with a Varian 9010 solvent delivery system, Varian 9050 variable wavelength UV-Visible detector and HP 3396 Series II integrator. The wavelength for the UV detector was 254 nm. The eluent for the HPLC assay on an Alltech Hypersil ODS C18 column (250 mm×4.6 mm; 5 micron; Stock# 9879) was 70% CH$_3$CN/2–% H$_2$O/10% THF. The flow rate was 0.7 mL/min and the column was at room temperature. Under those conditions the following elution times were obtained:

benzyl bromide—4.5 minutes; benzophenone—5.5 minutes; Schiff base substrate—7.2 mintues; benzylated product—11.1 minutes and perylene (internal standard)—12.5 minutes.

Determination of enantiomeric excess (%ee)

The ratio of enantiomers of the benzylated product was determined on a J. T. Baker Bakerbond chiral phase analytical DNBPG (covalent) HPLC column (250 mm×4.6 mm; 5 micron; Product #7113-0). The eluent consisted of 350:1 (volume/volume) of n-hexane and isopropanol with a flow rate of 0.3 mL/minute. Samples for analysis were filtered and then resuspended in the HPLC eluent at a concentration of 0.4 mg/mL.

Determination of initial rate. Determination of initial rates was done according to the method described by J. Algaranti in *J. Biochem. et Biophys. Acta* 1963, 73, 154.

SECTION IV. PREPARATION OF PREFERRED COMPOUNDS

In another set of experiments, preferred α-methyl tryptophan derivatives according to the following scheme were prepared using the indicated catalysts.

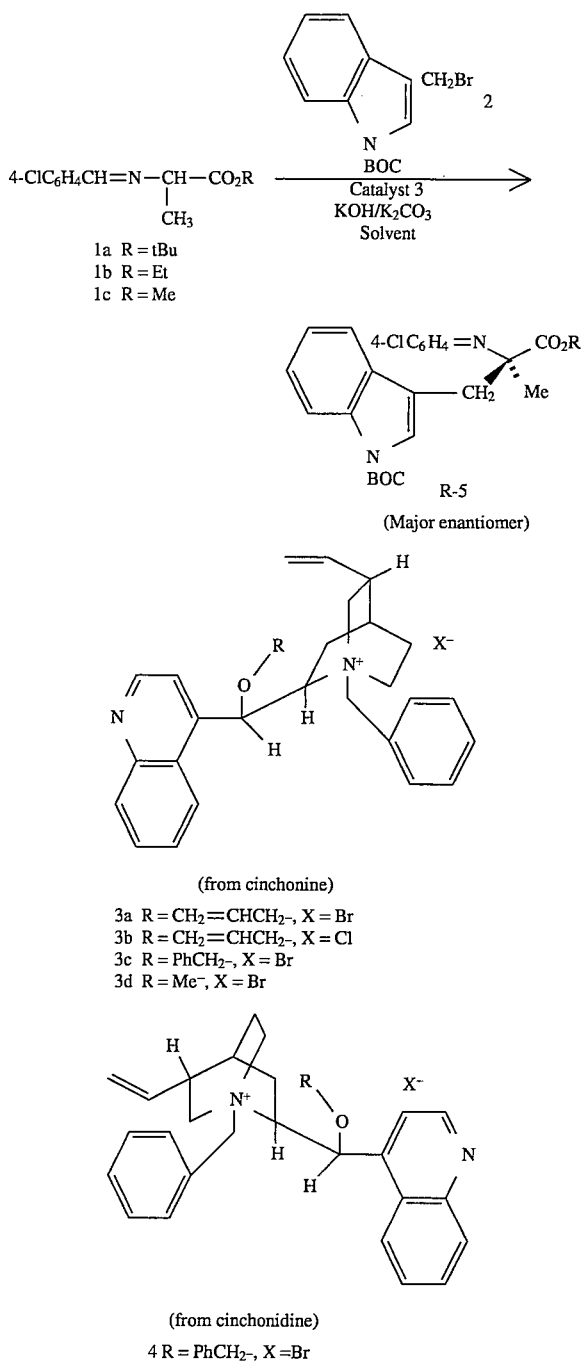

Synthesis of Alkyl N-[(4-chlorophenyl)methylene]alaninates (1) (General Procedure).

To a 250 mL round-bottom flask equipped with a drying tube was added p-chlorobenzaldehyde (2.18 g, 15 mmol), an equimolar amount of alkyl alaninate hydrochloride, magnesium sulfate (1.97 g, 16 mmol) and methylene chloride (75 mmol), followed by triethylamine (2.1 mL, 15 mmol). The resulting mixture was magnetically stirred for 24 hours at room temperature. The reaction mixture was filtered to remove solid materials ($NH_4Cl$, $MgSO_4$), and water (50 mL), separated and washed with water (2×40 mL), dried, filtered and evaporated to give a light yellow oil.

1. t-Butyl N-[(4-chlorophenyl)methylene]alaninate (1a) (3.82g, 97.9%)
2. Ethyl N-[(4-chlorophenyl)methylene]alaninate (1b) (1b) (3.45 g, 95.8%)
3. Methyl N-[(4-chlorophenyl)methylene]alaninate (1c) (3.46 g, 99.4%)

II. Synthesis of Alkyl Halide (2)
1. p-chlorobenzyl bromide

N-Bromosuccinimide (19 g, 0.107 mole) and benzoyl peroxide (2.5 g, 0.01 mole) were added to p-chlorotoluene (13 g, 0.103 mole) in carbon tetrachloride (100 mL). The reaction mixture was stirred and refluxed gently for 2 hours. When the succinimide rose to the surface, the reaction was finished. The solution was cooled to room temperature and the succinimide was filtered off. The filtrate was evaporated on a rotary evaporator. Then distillation gave p-chlorobenzyl bromide as colorless crystal (80° C.–85° C./1 mm Hg).

1-(tert-Butyloxycarbonyl)-3-(bromomethyl)indole (2)

(1) 1-(tert-Butyloxycarbonyl)-3-formylindole

Indole-3-carboxaldehyde (4.53 g, 30 mmol) was dissolved in tetrahydrofuran (100 mL) (dissolved at about 40° C.). Aqueous potassium hydroxide (1N, 30 mL) and tetrabutylammonium bromide (0.97 g, 3 mmol) were added. Then di-t-butylcarbonate (7.2 g, 33 mmol) was added (the temperature should not rise about 25° C.). The resulting mixture was stirred at room temperature until the starting material was not detected by TLC ($CH_2CL_2/CH_3OH$ 9:1). The reaction mixture was separated, and the aqueous layer was extracted with ethyl acetate (2×50 mL). The combined organic layer was dried with $MgSO_4$ and evaporated to give crude product. The product was recrystallized from methylene chloride/hexane (20 mL/100 mL) to obtain needle crystals (7.19 g, 97.7%). m.p. 124°–125° C.

(2) 1-(tert-Butyloxycarbonyl)-3-(hydroxymethyl)indole

To a 100mL two-necked round-bottom flask equipped with a thermometer 1-(tert-butyloxycarbonyl)-3-formylindole (13.7 g, 60 mmol) was suspended in ethanol (36 mL). Sodium borohydride (4.40 g, 115 mmol) was added in four portions, during which the temperature did not rise about 20° C., and the mixture was stirred for 6 hours. Then the solvent was evaporated in vacuo. The residual oil was shaken with 1.0N sodium hydroxide (150 mL), and the alkaline solution was extracted with ether (3×180 mL), dried with $MgSO_4$, filtered and evaporated to give a colorless oil which solidified on refrigeration (3.95 g, ca. 100%).

(3) 1-(tert-Butyloxycarbonyl)-3-(bromomethyl) indole (2)

To a 250 mL three-necked round-bottom flask equipped with a gas bubbler was added dibromotriphenylphoshorane (5.06 g, 12 mmol). Then the apparatus was flushed with argon. Dry carbon tetrachloride (90 mL, distilled from the solution after reflux with $P_2O_5$ for 18 hours) was added using a syringe. A solution of 1-(tert-butyloxycarbonyl)-3-(hydroxymethyl)indole (2.7g, 11 mmol) dissolved in carbon tetrachloride (20 mL) was added dropwise during one hour. The reaction mixture was then stirred for 3 days at room temperature under Ar. The reaction slurry was filtered through a 0.5–×3– cm pad of celite wetted with carbon tetrachloride to remove triphenylphosphane. The filtrate was evaporated to dryness and the solid residue was treated with hexane (400 mL), filtered and the hexane evaporated. This procedure was repeated to remove residual triphenylphosphane to give a white powder (2) (3.2 g, 94.6%).

III Synthesis of Chiral Phase Transfer Catalysts

1. N-Benzyl-O-Allyl Cinchoninium Chloride (3b)

To a 100 mL round-bottom flask were added N-benzyl cinchoninium chloride (1.68 g, 4 mmol), allyl bromide (0.74 g, 6 mmol) and methylene chloride (40 mL), followed by 50% aqueous sodium hydroxide (3.2 g, 80 mmol). The resulting mixture was stirred vigorously at room temperature for 2 hours. The reaction mixture was transferred to a separatory funnel and the aqueous layer was separated. The organic layer was washed with water (2×10 mL), dried (MgSO$_4$), filtered and evaporated in vacuo to dryness to give a yellow solid. The solid was suspended in ether (80 mL), stirred overnight, and filtered to give crude product. It was dissolved in methylene chloride (5 mL) and purified by liquid vacuum chromatography over aluminium oxide (35 g of activated basic Brockman from Aldrich Chem. Co. aluminium oxide standard grade, 150 mesh surface area 155 m$^2$/g, 58A), using as eluent, first hexane (40 mL) then chloroform (3×50 mL) to obtain light yellow crystals of 3b (1.51 g, 82.1%).

2. N,O-Dibenzyl Cinchoninium Bromide (3c)

To a 250 mL round-bottom flask was added cinchonine (2.36 g, 8 mmol), methylene chloride (80 mL) and benzyl bromide (2.1 mL, 17.6 mmol), followed by 50% aqueous sodium hydroxide (6.4 g, 17.6 mmol). The resulting mixture was stirred until then layer chromatography indicated complete reaction. The reaction mixture was transferred to a separatory funnel and the aqueous layer was separated. The organic layer was washed with water (2×20 mL), dried over magnesium sulfate, filtered and evaporated in vacuo to dryness. The residue was suspended in ether (80 mL), stirred overnight, and filtered to give crude product (4.85 g). The crude product was purified by two different methods. One portion of the crude product (3 g) was purified by column chromatography on 2.0×20 cm silica gel (60, 230–400 mesh) using 1% methanol/99% dichloromethane as eluent to obtain light yellow crystals of 3c (2 g, 67%). The other portion of the crude product (1.35 g) was purified by liquid vacuum chromatography over aluminium oxide (20 g of activated basic Brockman from Aldrich Chem. co. aluminium oxide standard grade, 150 mesh surface area 155 m$^2$/g, 58A), using chloroform as eluent to obtain light yellow crystals of 3c (0.98 g, 72.6%), m.p. 159°–162° C.

3. N,O-Dibenzyl Cinchonidinium Bromide (4)

To a 500 mL round-bottom flask were added cinchonidine (9.44 g, 32 mmol), methylene chloride (320 ml) and benzyl bromide (8.5 mL, 71 mmol), followed by 50% aqueous sodium hydrocide (25.6 g, 640 mmol). The resulting mixture was stirred vigorously at room temperature for 3 hours. The reaction mixture was transferred to a separatory funnel, the layers were separated and the organic layer was washed with water (2×80 mL), dried (MgSO$_4$), filtered and evaporated in vacuo to dryness. The residue was suspended in ether (80 mL), stirred overnight, and filtered to give the crude product (16 g). The crude product was purified by liquid vacuum chromatography over aluminium oxide (150 g of activated basic Brockman from Aldrich Chem. Col. aluminium oxide standard grade (150 mesh surface area 155 m$^2$/g, 58A), chloroform (600 mL) as eluent. The solution was evaporated in vacuo to give a light yellow solid (15 g, 90%). The product was recrystallized from methylene chloride/acetone (120 mL/200 mL), and filtered to yield 11–12 g of white powder. (chemical yield 60–65%), m.p. 205°–206° C.

IV. Asymmetric Dialkylation by Catalytic Enantioselective PCT

General Procedure:

Alkyl N[(4-chlorophenyl)methylene]alaninate (1 mmol) and 1-(tert-butyloxycarbonyl)-3-bromomethyl)indole (1.05 mmol) and toluene (7 mL)/methylene chloride (3 mL) were added to a 100 mL three-necked round-bottom flask with mechanical stirring, followed by O-allyl-N-benzylcinchoninium chloride (0.1 mmol), ground potassium carbonate (1.38 g, 10 mmol) and potassium hydroxide (0.56 g, 10 mmol). The resulting mixture was stirred for 4 hours at room temperature under Argon. Then the reaction slurry was filtered through a 0.2–×2.5– cm pad of celite wetted with methylene chloride. The filtrate was evaporated to dryness. The residue was dissolved in ether (20 mL), washed with water (2×10 mL), dried with MgSO$_4$ and evaporated to give an orange oil.

1. Asymmetric dialkylation to yield R-5a Chemical yield: 85–100%; Optical yield 74–76%
2. Asymmetric dialkylation to yield R-5b Chemical yield ca. 100%; Optical yield 42%
3. Asymmetric dialkylation to yield R-5c Chemical yield ca. 100%; Optical yield 37.2%

The results of testing using these various catalysts and substrates are summarized in Tables 3 to 6 below.

TABLE 3

Effect of Different Chiral Catalysts on Asymmetric Dialkylation

| Subst. | Subst. (mmol) | Cat. | Solvent (mL) | Reaction time (h) | % C.Y. | % ee |
|---|---|---|---|---|---|---|
| 1a | 0.9 | 3a | CH$_2$Cl$_2$ (2) | 24 | 97 | 43 |
| 1a | 0.9 | 3b | CH$_2$Cl$_2$ (2) | 24 | 90 | 44 |
| 1a | 0.9 | 3c | CH$_2$Cl$_2$ (2) | 24 | 90 | 39 |
| 1a | 0.9 | 3d | CH$_2$Cl$_2$ (2) | 24 | 86 | 38 |

TABLE 4

Solvent Effects on the Asymmetric Dialkylation

| Subst. | Subst. (mmol) | Cat. | Solvent (mL) | Reaction time (h) | % e.e. |
|---|---|---|---|---|---|
| 1a | 0.9 | 3a | CH$_2$Cl$_2$ (10) | 42 | 51 |
| 1a | 0.9 | 3a | CH$_2$Cl$_2$ (2) | 24 | 43 |
| 1a | 0.9 | 3a | Toluene (9) CH$_3$CN (1) | 42 | 46 |
| 1a | 0.9 | 3a | Toluene (9) CH$_2$Cl$_2$ (1) | 42 | 69 |
| 1a | 0.9 | 3a | Toluene (8) CH$_2$Cl$_2$ (2) | 42 | 71 |
| 1a | 0.9 | 3a | Toluene (7) CH$_2$Cl$_2$ (3) | 42 | 71 |
| 1a | 0.9 | 3a | Toluene (7) CH$_2$Cl$_2$ (3) | 42 | 76 |

TABLE 5

Asymmetric Dialkylation of Different Schiff Base Esters

| Subst. | Subst. (mmol) | Cat. | Solvent (mL) | Reaction time (h) | % e.e. |
|---|---|---|---|---|---|
| 1a | 0.9 | 3b | Toluene (7) CH$_2$Cl$_2$ (3) | 4 | 75 |
| 1b | 0.9 | 3b | Toluene (7) CH$_2$Cl$_2$ (3) | 4 | 37 |
| 1c | 0.9 | 3b | Toluene (7) CH$_2$Cl$_2$ (3) | 4 | 42 |

TABLE 6

Asymmetric Dialkylation with Mechanical Stirring

| Subst. | Subst. (mmol) | Cat. | Solvent (mL) | Reaction time (h) | % e.e. |
|---|---|---|---|---|---|
| 1a | 0.9 | 3b | Toluene (7) $CH_2Cl_2$ (3) | 0.5 | 73 |
| 1a | 0.9 | 3b | Toluene (7) $CH_2Cl_2$ (3) | 1.5 | 75 |
| 1a | 0.9 | 3b | Toluene (7) $CH_3CN$ (3) | 2.5 | 76 |
| 1a | 0.9 | 3b | Toluene (7) $CH_2Cl_2$ (3) | 3.5 | 76 |
| 1a | 0.9 | 3b | Toluene (28) $CH_2Cl_2$ (12) | 4.0 | 75 |
| 1a | 0.9 | 3b | Toluene (28) $CH_2Cl_2$ (12) | 4.0 | 76 |

While the invention has been illustrated and described in detail in the foregoing description, the same is to be considered as illustrative and not restrictive in character, it being understood that only the preferred embodiments lave been described and that all changes and modifications that come within the spirit of the invention are desired to be protected.

All publications cited herein are indicative of the level of skill in the art and are hereby incorporated herein by reference as if each had been individually incorporated by reference and fully set forth.

What is claimed is:

1. A compound useful as an enantioselective catalyst, comprising an N-substituted O-substituted cinchoninium or cinchonidinium halide or a 3a,3b-dihydro N-substituted O-substituted cinchoninium or cinchonidinium halide, wherein the N-substituent is alkyl-aryl wherein the alkyl is $C_1$ to $C_5$ and the aryl is up to $C_{30}$, and the O-substituted is $C_1$ to about $C_{10}$ alkyl or alkenyl.

2. The compound of claim 1 wherein the O-substituted is is allyl, methyl, ethyl, propyl or butyl.

3. The compound of claim 2 wherein the O-substituent is allyl.

4. The compound of claim 2 wherein the N-substituent is —$(CH_2)_y$—Phe where y is 1 to 5 and Phe is phenyl.

5. The compound of claim 4 wherein the N-substituent is benzyl.

6. The compound of claim 2 which is a cinchoninium or cinchonidinium bromide or chloride.

7. The compound of claim 4 which is a cinchoninium or cinchonidinium bromide or chloride.

* * * * *

UNITED STATES PATENT AND TRADEMARK OFFICE
CERTIFICATE OF CORRECTION

PATENT NO. : 5,554,753

DATED : September 10, 1996

INVENTOR(S) : Martin J. O'Donnell et al.

It is certified that error appears in the above-indentified patent and that said Letters Patent is hereby corrected as shown below:

In col. 2, line 62, please insert an ampersand in between "Chemical" and "Engineering".

In col. 4, line 10, please delete both instances of "R" and insert in lieu thereof $--R^5--$.

In col. 4, line 24, please delete "$R^1$" and insert in lieu thereof $--R^5--$.

In col. 6, line 35, please delete "CH2" and insert in lieu thereof $--CH_2--$.

In col. 7, line 29, please delete "R5" and insert in lieu thereof $--R^5--$.

In col. 14, line 46, please delete "5%" and insert in lieu thereof --15.5%--.

In col. 14, line 64, please delete "benzyl-N" and insert in lieu thereof --benzyl N--.

In col. 15, line 30, please delete "mole" and insert in lieu thereof --mmole--.

In col. 15, line 47, please insert a closed bracket symbol after "methylene", but before the hyphen.

In col. 16, line 19, please delete the "(" before the alpha symbol.

In col. 16, line 23, please delete "mole" and insert in lieu thereof --mmole--.

In col. 18, line 14, please delete "$CH_2C_2$" and insert in lieu thereof $--CH_2Cl_2--$.

In col. 20, line 26, please insert --2. -- before "1-(tert-".

UNITED STATES PATENT AND TRADEMARK OFFICE
CERTIFICATE OF CORRECTION

PATENT NO. : 5,554,753
DATED : September 10, 1996
INVENTOR(S) : Martin J. O'Donnell et al.

It is certified that error appears in the above-identified patent and that said Letters Patent is hereby corrected as shown below:

In col. 24, lines 9 and 11, please delete "O-substituted" and insert in lieu thereof --O-substituent--.

Signed and Sealed this

Twenty-fourth Day of February, 1998

*Attest:*

BRUCE LEHMAN

*Attesting Officer*    *Commissioner of Patents and Trademarks*